United States Patent [19]

Schmitz et al.

[11] Patent Number: 4,743,695

[45] Date of Patent: May 10, 1988

[54] TEDANOLIDE

[75] Inventors: Francis J. Schmitz, Norman, Okla.; Sarath P. Gunasekera, Vero Beach, Fla.; M. Bilayet Hossain; Dick van der Helm, both of Norman, Okla.; Gopichand Yalamanchili, St. Louis, Mo.

[73] Assignee: The Board of Regents for the University of Oklahoma, Norman, Okla.

[21] Appl. No.: 7,347

[22] Filed: Jan. 27, 1987

Related U.S. Application Data

[63] Continuation-in-part of Ser. No. 577,705, Feb. 8, 1984, abandoned.

[51] Int. Cl.$^4$ ............................................. C07D 313/00
[52] U.S. Cl. .................................................. 549/271
[58] Field of Search ......................................... 549/271

[56] References Cited

U.S. PATENT DOCUMENTS 4,302,470 11/1981 Schmitz et al. ..................... 549/90
4,314,057 2/1982 Schmitz et al. ..................... 549/90
4,493,796 1/1985 Rinehart, Jr. ................. 260/112.5 R

OTHER PUBLICATIONS

"Chemical Structures of Interest to the Division of Cancer Treatment", vol. III, Lomax, et al., pp. 15–16, Jan. 1983.

J. Am. Chem. Soc., "Isolation and Structure of Bryostatin 1", Pettit, et al., pp. 6846–6848, 1982.

J. Natural Products, vol. 46, No. 4, Jul./Aug. 1983, "The Structure of Bryostatin 2 from the Marine Bryozoan Bugula Neritina", Pettit, et al., pp. 528–531.

Pharm. Mfg. Encyclo. Chem. Tech. Review No. 124, Noyes Data Corp., Park Ridge, N.J., 1979, "Erythromycin", pp. 231–234.

Angew. Chem. Int. Ed. Engl. 16, 1977, "Macrolides. Recent Progress in Chemistry and Biochemistry", Masamune, et al., pp. 585–607.

Primary Examiner—Jane T. Fan
Attorney, Agent, or Firm—Dunlap, Codding & Peterson

[57] ABSTRACT

A compound having cytotoxic activity of the formula:

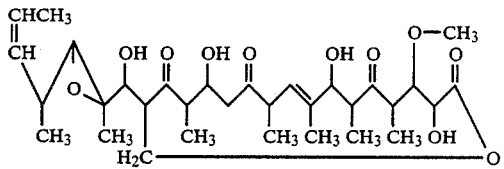

and a composition comprising such compound in a suitable pharmaceutical carrier.

2 Claims, 4 Drawing Sheets

300 MHz $^1$H NMR SPECTRUM OF TEDANOLIDE IN $CDCl_3$

TEDANOLIDE

○ CARBON
◍ OXYGEN
∘ HYDROGEN

TEDANOLIDE

This patent application is a continuation-in-part of co-pending application U.S. Ser. No. 577,705, filed Feb. 8, 1984, entitled "TEDANOLIDE: A NEW ANTI-CANCER AND ANTIBIOTIC COMPOUND" now abandoned.

FIELD OF THE INVENTION

The present invention relates generally to bioactive compounds and in particular to a compound called tedanolide which is derived from marine sponges.

SUMMARY OF THE INVENTION

The present invention comprises a compound of the formula:

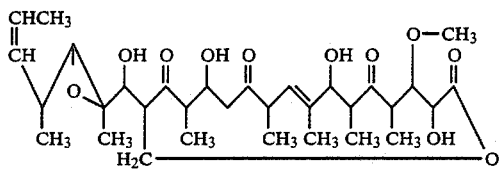

The present invention further comprises a composition comprising the above-identified compound dissolved in a suitable carrier, wherein the compound is present in a cytoxically effective amount.

The present invention further comprises a method for isolating tedanolide involving extracting tedanolide from sponges of the genus Tedania with a solution comprising an organic solvent to produce a tedanolide extract and separating tedanolide from the tedanolide extract.

DESCRIPTION OF THE PREFERRED EMBODIMENT

Figure 1:
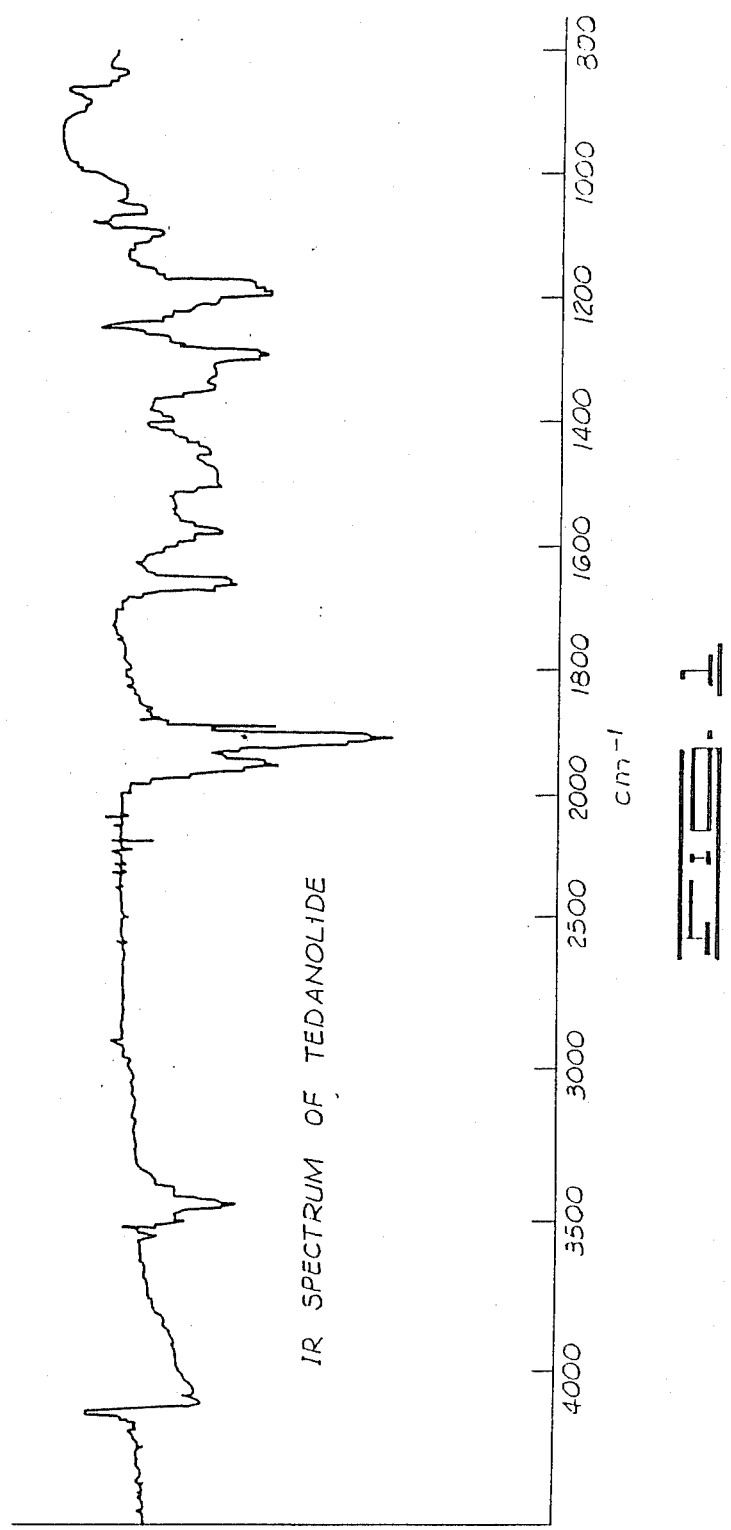
FIG. 1 is an infrared spectrum of tedanolide.

The compound of the present invention named "TEDANOLIDE" has the following general structure:

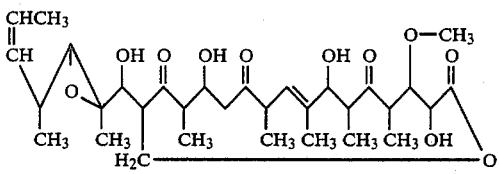

Tedanolide may be synthesized or may be isolated from marine sponges. Suitable sponges include the species *Tedania ignis*, of the genus Tedania. Tedanolide also may be extracted from populations of algae and microorganisms living within such marine sponges.

The marine sponges from which tedanolide may be isolated may be collected manually. However, it is to be understood that any suitable method for collecting such sponges, such as dredging or via a suitable submersible vessel, are also within the scope of the present invention.

In order to obtain workable quantities of tedanolide, approximately 1 to 100 pounds of sponges are cut into pieces of a size which allows thorough and convenient extraction. Suitable convenient sizes include 1 cm$^3$ to about 5 in$^3$.

After being cut, the sponges may be used immediately, or may be frozen, freeze-dried or preserved in a suitable medium. The preserving medium may be a common organic solvent. Suitable solvents include alcohols, such as ethanol and isopropanol, acetone and mixtures of these with chloroform, benzene or ethyl acetate. Freeze-dried specimens may be extracted with methylene chloride, chloroform, benzene, ethyl acetate, acetone or low molecular weight alcohols. The sponge extracts are fractionated by solvent partitioning in order to obtain fractions differing substantially in polarity. These fractions may be further purified to obtain pure compounds. As used herein, the words "purified" and "pure" are meant to indicate materials comprising at least 90% to 95% tedanolide, and preferably more than 99% tedanolide.

The pertinent fraction may be obtained by extraction of the concentrated crude extract (usually diluted with some water) with a solvent such as an alkane, methylene chloride, chloroform, carbon tetrachloride, ethyl acetate, benzene or a mixture thereof, applied either in combinations or sequentially. Generally, any low molecular weight, volatile, somewhat polar, water-immiscible solvent or mixture of solvents would be suitable. Suitable alkanes include pentane, hexane, heptane, isooctane or mixtures thereof.

The organic solubles from such an extraction may be subjected to a series of solvent partitions to further concentrate tedanolide. This may be done by dissolving these organic solubles in methanol-water (approximately 9:1) and partitioning the resulting solution successively against hexane, carbon tetrachloride, and chloroform, the water content in the methanol phase being increased after the hexane and carbon tetrachloride extractions to give methanol-water mixtures of approximately 8:2 and 7:3, respectively. Other water soluble alcohols or a different series of increasingly polar water-immiscible organic solvents may be used.

The initial extraction and subsequent ones may be effected by percolation, Soxhlet extraction, continuous liquid-liquid extraction, or counter-current extraction (solvent partitioning). The final separation of the compound is accomplished by conventional chromatographic techniques. Suitable chromatographic techniques include open column or dry column adsorption chromatography, partition chromatography, preparative thin layer chromatography, high pressure liquid chromatography (adsorption or reverse phase), droplet counter-current chromatography, gel permeation chromatography, or ion exchange chromatography.

Suitable adsorbents used in the chromatography include dextran based adsorbents such as Sephadex LH-20 or Sephadex G10 to G200, silica gel, alumina, polymer beads such as polyamide or polystyrene beads, DEAE cellulose, florisil or magnesol.

In a preferred extraction procedure, about 25 to 75 pounds of the sponge *Tedania ignis*, which can be obtained from many places in the Caribbean region, such as in the Florida Keys, Bimini, the Bahamas or Puerto Rico, are initially extracted with chloroform-methanol or a low MW alcohol such as methanol, ethanol, isopropanol or butanol. This initial extractant is then concentrated in order to remove the alcohol or methanol/chloroform. It is preferable to evaporate the extraction solvent(s) at a reduced pressure in order to lower the temperature of the boiling solution. The boiling temperature is preferably kept below 50° C. The resulting concentrate is extracted step-wise or continuously with the water-immiscible organic solvent as discussed above.

One or several portions of each extractant may be used. The concentrate may be extracted with one solvent or with a series of solvents. One preferable series includes methylene chloride or chloroform, then n-butyl alcohol.

BIOLOGICAL ACTIVITY

The presently disclosed compounds have cytotoxic and in vivo anti-tumor activity. National Cancer Institute (NCI) protocols specify that a compound is considered "active", i.e., to have significant cytotoxic activity, if the compound at a concentration of 10 mcg/ml in the cell suspension inhibits by 50% the growth of cancer cells raised in cell culture. This is referred to as an Effective Dose 50 (ED50) of 10 mcg/ml. The compounds that are effective in inhibiting by 50% the growth of cancer cells at an even lower concentration are considered more active. Tedanolide exhibited an ED50 of 0.00025 mcg/ml against the NCI's KB cell line (a human carcinoma of the nasopharynx) and an ED50 of 0.000016 mcg/ml against the PS cell line (lymphocytic leukemia). Since far less tedanolide is needed to cause 50% inhibition of cancer cells in tissue culture than the criteria set by NCI (10 mcg/ml), tedanolide is shown to be an effective cytotoxic compound.

In in vivo tests conducted with mice implanted with lymphocytic leukemia (PS) cells, tedanolide administered at a dose of 1.56 mcg/KG caused an increase in lifetime of 23% over that of controls. For a compound to be considered active in this test, the NCI specifies that a compound should increase by 25% or more the lifetime of test mice; hence, tedanolide shows borderline activity in this test system. When tested similarly against NCI's M5 (ovarian cancer) cell line, tedanolide was inactive. Tedanolide was toxic to mice in the 12–40 mcg/ml range.

In order to use the compounds of the present invention as antitumor, cytotoxic or antibiotic agents or potentially to improve the utilization of ruminant feed by alteration of microbial flora, the compounds may be used in their substantially pure states or may be combined with suitable pharmaceutical carriers. In such compositions, the purified compounds of this invention can be used in combinations containing about 1% to 99% by weight.

Suitable pharmaceutical carriers include salts such as saline solution, ethyl alcohol, glycols such as ethylene glycol, sugars, methyl cellusolve, and topical carriers such as alcohols, cremes, ointments, salves or balms containing suitable ingredients such as oils, fats and the like.

The compound or pharmaceutical composition may be topically applied, such as to the surface of a tumor or lesion, or may be administered orally, intraperitoneally or intravenously.

The compounds are administered in effective, nontoxic amounts, suitably 0.001–100 mg per day per kg of body weight.

Having generally described the invention, a more complete understanding can be obtained by reference to certain specific examples, which are provided herein for purposes of illustration only, and are not intended to be limiting unless otherwise specified.

EXAMPLE 1

Figure 2:
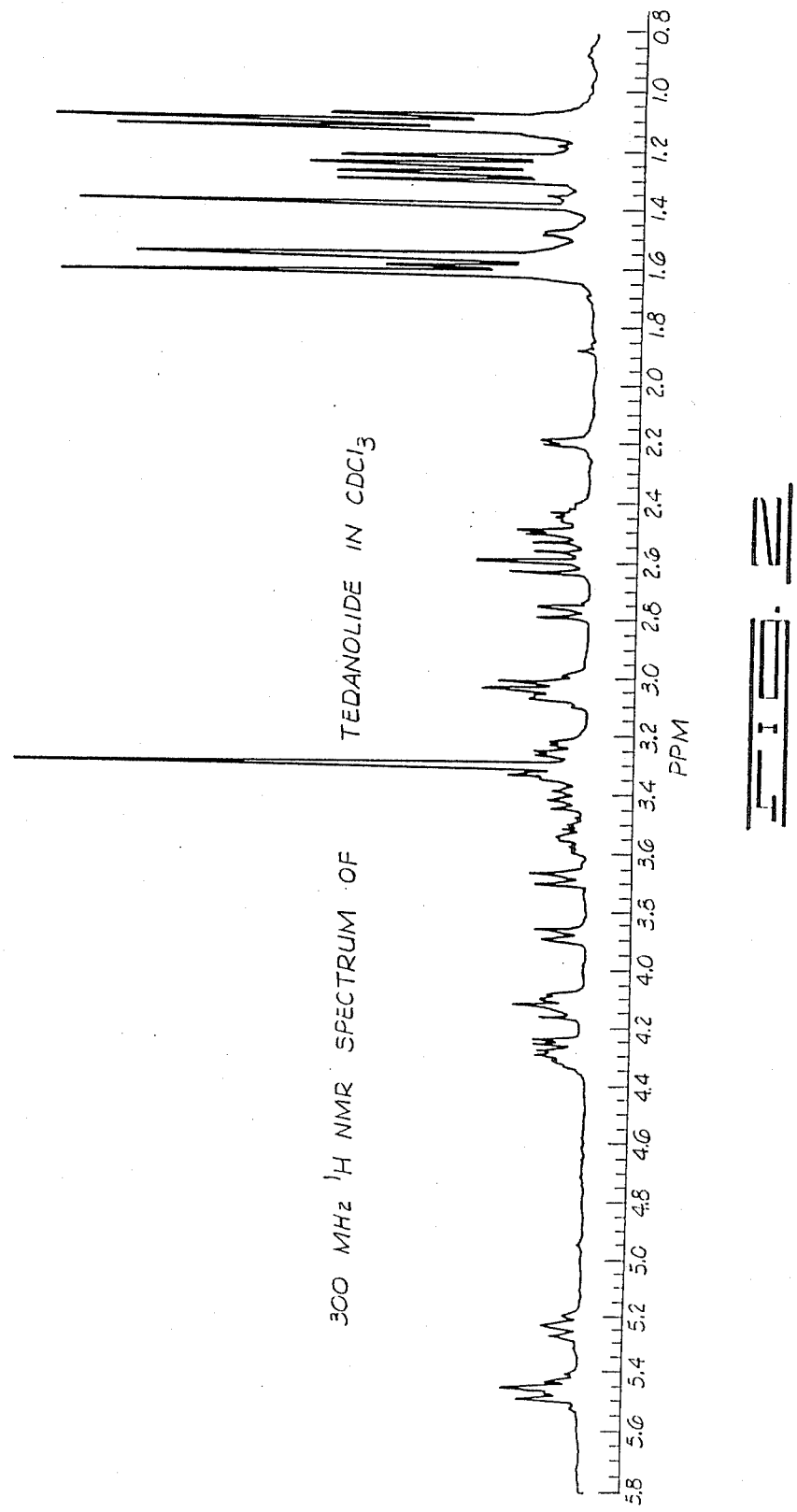
FIG. 2 is an $^1$H nuclear magnetic resonance spectrum of tedanolide at 300 MHz using CDCl$_3$ as a solvent.
Figure 3:
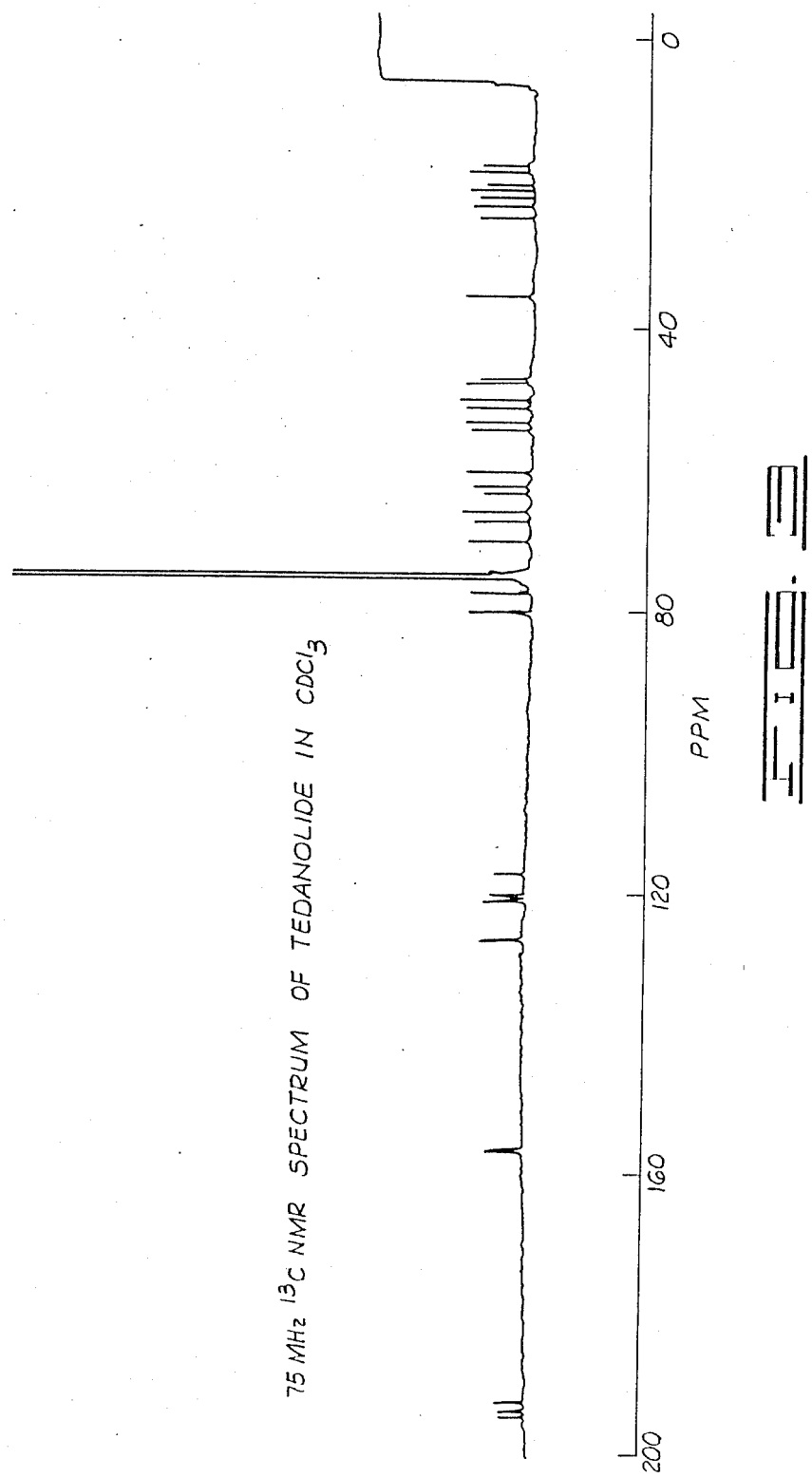
FIG. 3 is a carbon-13 nuclear magnetic resonance spectrum of tedanolide obtained at 75 MHz in CDCl$_3$.

Freeze-dried specimens (1517.49 g) of *Tedania ignis* were broken into small pieces and extracted twice by soaking in $CH_2Cl_2$ for 1–2 days. Evaporation of the $CH_2Cl_2$ gave a residue of 105.24 g which was then dissolved in 1500 ml of methanol-water (90:10) and extracted with three portions of hexane (1500, 750 and 750 ml, respectively). The aqueous methanol layer was diluted with water (150 ml) to produce an approximately 80:20 methanol:water solution, and this was then extracted with three portions of $CCl_4$ (1500, 750 and 750 ml, respectively). More water (150 ml) was added to the aqueous methanol fraction to increase the water content to approximately 30%, and this solution was extracted with three portions of $CHCl_3$ (1500, 750 and 750 ml, respectively). The $CHCl_3$ and $CCl_4$ fractions were combined (7.78 g) and chromatographed over a Sephadex LH-20 column (2"×35") using $CHCl_3$—$CH_3OH$ (1:1) as eluant. Fractions, each containing about 55 ml, were collected. Combined fraction numbers 7 to 11, after evaporation, contained a residue of approximately 2.5 g. The residue was chromatographed over 100 g of 230–400 mesh silica gel (deactivated with 15 ml of water in 300 ml of $CH_3OH$) collecting 100 ml fractions using gradient elution beginning with $CHCl_3$ and progressing to 10% $CH_3OH$—$CHCl_3$. Fraction numbers 15 and 16, which were eluted with 5% $CH_3OH$ in $CHCl_3$, contained an evaporative residue of 58 mg. This residue was subjected to high pressure liquid chromatography (hplc) using a silica gel column (9 mm I.D.×25 cm; 10 micron particles) with 2% $CH_3OH$—$CHCl_3$ as eluant and separated into 6 fractions. The third fraction, with 6.8 mg of evaporative residue, was subjected to hplc using a reversed phase C-18 radial compression column (8 mm I.D.×10 cm; 10 micron particles) with 20% aqueous methanol eluant and separated into four fractions. The 2.5 mg evaporative residue from fraction 2 was purified further by hplc using a 9 mm×25 cm (10 micro particles) silica gel column with 2% $CH_3OH$—$CHCl_3$ eluant to give 1.7 mg of pure tedanolide, having a melting point of 190°–191° C. (decomp.) when crystallized from $CHCl_3$. The infrared spectrum of pure tedanolide is shown in FIG. 1. The $^1H$ nuclear magnetic resonance spectrum of pure tedanolide is shown in FIG. 2. The carbon-13 nuclear magnetic resonance spectrum of pure tedanolide is shown in FIG. 3.

EXAMPLE 2

About 40 pounds of *Tedania ignis* which had been frozen immediately after collection and preserved at −10° C. was partially thawed and then immersed in 20 L of $CH_3OH$—$CHCl_3$ (1:1) and left at room temperature for 3 days. The liquid was recovered by decantation and filtration and then concentrated on a flash evaporator. The undissolved sponge residue thus obtained was next soaked twice in chloroform at room temperature for 4-day periods. The resulting chloroform extracts were concentrated on a rotary evaporator and finally all three crude extracts were combined and evaporated to dryness in vacuo using a water bath at 40° C. to give 50 g of residue. This residue was dissolved in 3 L of H₂O—CH₃OH (10:90), and the resulting solution was extracted with two 1 L portions of hexane. Water (600 ml) was added to the aqueous methanol solution to give an approximately 30% H₂O—70% methanol solution and this was extracted with two portions of CHCl₃ (1500 ml ea.). The combined CHCl₃ extracts were evaporated to dryness in vacuo on a water bath at 40° C. to give a residue of approximately 24 g. This residue was chromatographed in three equal portions over a Sephadex LH-20 column (2"×35") using CHCl₃—CH₃OH (1:1) as eluant. Fractions of approximately 75 ml were collected. Fractions 6 and 7 from the three separate chromatographies were combined and evaporated to give a residue of approximately 4.5 g. This residue was chromatographed over 250 g of 230–400 mesh silica gel (deactivated with 25 ml of water in 250 ml of methanol) using gradient elution (60 ml fractions) beginning with CHCl₃ and progressing to 5% CH₃OH—CHCl₃. Fraction 19, which was eluted with about 5% CH₃OH—CHCl₃ and contained 112 mg of residue, was subjected to hplc using a silica gel column (9 mm I.D.×25 cm; 5 micron particles) with 4% CH₃OH—CHCl₃ as eluant and thus separated into 5 fractions. Fractions 2–4 were combined and evaporated to dryness to give a residue of approximately 6 mg. This residue was purified further by hplc using a reversed phase C-18 column (5 micron particles; 9 mm I.D.×25 cm) with a mobile phase of H₂O—CH₃OH (35:65) to give 2.0 mg of pure tedanolide. Crystallization of tedanolide from several preparations from benzene-d₆-CDCl₃ (9:1) (0.25 ml) yielded approximately 4 mg of white crystals, [mp; 193°–194° C. (decomp.); (α)_D+18.7° (c. 0.08, CHCl₃)]. One of these crystals was used for the x-ray structure determination.

DETERMINATION OF STRUCTURE BY X-RAY DIFFRACTION

Figure 4:
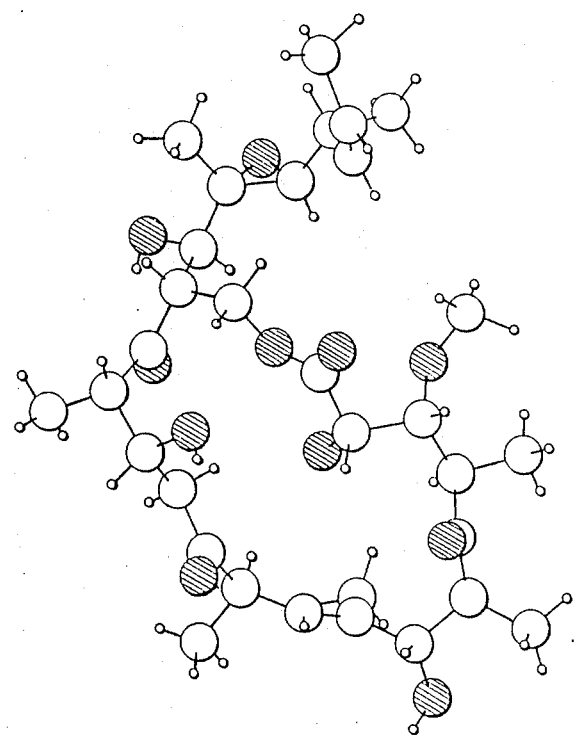
FIG. 4 shows a perspective view of the structure of tedanolide.

The structure of tedanolide was determined by x-ray diffraction. A nearly cubic-shaped crystal (0.19×0.20×0.24 mm) was selected for all x-ray measurements. Tedanolide crystallizes in the orthorhombic space group P2₁2₁2₁ with a=16.084(7)Å, b=29.850(20)Å, c=6.671(4)Å, V=3202.8A³, Z=4. Cell parameters were obtained by a least-squares fit to ±20 of 48 reflections measured at 138K using CuKα₁ radiation. Intensities of all unique reflections with 2θ≦150 were collected on an EnrafNonius CAD-4 automatic diffractometer at 138±2K using Ni-filtered CuK⁻α radiation. θ-2θ scan technique was employed using variable scan width (0.70+0.20 tan θ)°, and a variable horizontal aperture (3.5+0.86 tan θ) mm. Intensities of three standard reflections were monitored every 2 hours and crystal orientation was checked after every 200 measurements. Out of the total of 3792 reflections, 2996 reflections had intensities greater than 2 times their estimated standard deviations. The structure was determined by the direct methods and successive difference Fourier syntheses. The preliminary structure (assuming all carbon atoms) was refined by least-squares using isotropic thermal parameters. Subsequently, the oxygen atoms were identified by scrutinizing the molecular geometry and the individual atomic thermal parameters. Refinement was continued with anisotropic thermal parameters to an R factor of 0.082. All 50 hydrogen atoms in the molecule were located from a difference Fourier map and these atoms were refined isotropically. The refinement converged to a final R factor of 0.042 for 2996 observed reflections. A perspective view of the tedanolide molecule is shown in FIG. 4.

Having now fully described the invention, it will be apparent to one of ordinary skill in the art that many changes and modifications can be made thereto without departing from the spirit or scope of the invention as set forth herein.

What is claimed is:

1. A compound of the formula:

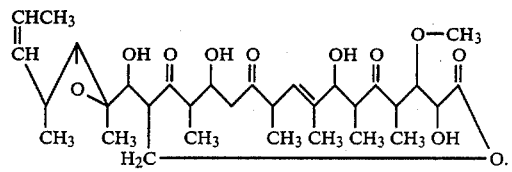

2. A composition comprising:
a cytotoxically effective amount of a compound of the formula:

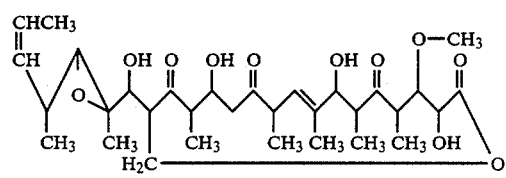

and
a pharmaceutical carrier.

* * * * *